United States Patent
Ellrich et al.

(10) Patent No.: US 8,965,518 B2
(45) Date of Patent: Feb. 24, 2015

(54) DEVICE AND METHOD FOR APPLYING A TRANSCUTANEOUS ELECTRICAL STIMULATION TO THE SURFACE OF A SECTION OF THE HUMAN EAR

(71) Applicant: cerbomed GmbH, Erlangen (DE)

(72) Inventors: Jens Ellrich, Langensendelbach (DE); Christoph Beck, Moehrendorf (DE); Wolf Gerhard Frenkel, Inzigkofen-Engelswies (DE); Andreas Hartlep, Holzkirchen (DE)

(73) Assignee: cerbomed GmbH, Erlangen (DE)

( * ) Notice: Subject to any disclaimer, the term of this patent is extended or adjusted under 35 U.S.C. 154(b) by 0 days.

(21) Appl. No.: 14/057,409

(22) Filed: Oct. 18, 2013

(65) Prior Publication Data
US 2014/0046406 A1    Feb. 13, 2014

Related U.S. Application Data

(63) Continuation of application No. PCT/EP2012/001633, filed on Apr. 16, 2012.

(30) Foreign Application Priority Data

Apr. 19, 2011   (DE) .................. 10 2011 018 228

(51) Int. Cl.
*A61N 1/00* (2006.01)
*A61B 5/04* (2006.01)
(Continued)

(52) U.S. Cl.
CPC ........ *A61N 1/36053* (2013.01); *A61N 1/36032* (2013.01); *A61N 1/0476* (2013.01); *A61H 2201/165* (2013.01); *A61N 1/36014* (2013.01); *A61H 39/002* (2013.01);
(Continued)

(58) Field of Classification Search
USPC ............................ 607/55, 62, 136; 600/372
See application file for complete search history.

(56) References Cited

U.S. PATENT DOCUMENTS

| 3,659,614 A | 5/1972 | Jankelson |
| 6,341,237 B1 | 1/2002 | Hurtado |

(Continued)

FOREIGN PATENT DOCUMENTS

| DE | 10 2010 015 278 A1 | 10/2011 |
| DE | 10 2010 054 165 B3 | 5/2012 |
| WO | 92/08516 A1 | 5/1992 |

(Continued)

*Primary Examiner* — Nicole F Lavert
(74) *Attorney, Agent, or Firm* — Lucas & Mercanti, LLP

(57) ABSTRACT

The invention relates to a device for applying a transcutaneous electrical stimulation stimulus to the surface of a section of the human ear, which comprises a retaining element which is mountable on or in the ear and a number of electrodes which are arranged on or in an electrode carrier, wherein the device comprises a control apparatus which controls or regulates the generation of a potential difference between the electrodes. In order to permit an improved and safer transcutaneous stimulation the invention proposes that at least three electrodes are arranged on or in the electrode carrier, wherein the at least three electrodes are located in one plane, wherein the position of at least one of the at least three electrodes is adjustable on the electrode carrier and wherein the at least one electrode of which the position is adjustable is mounted such as to be displaceable in a translational manner in the plane. Furthermore, the invention relates a method for the operation of such a device.

10 Claims, 3 Drawing Sheets

Figure 1:
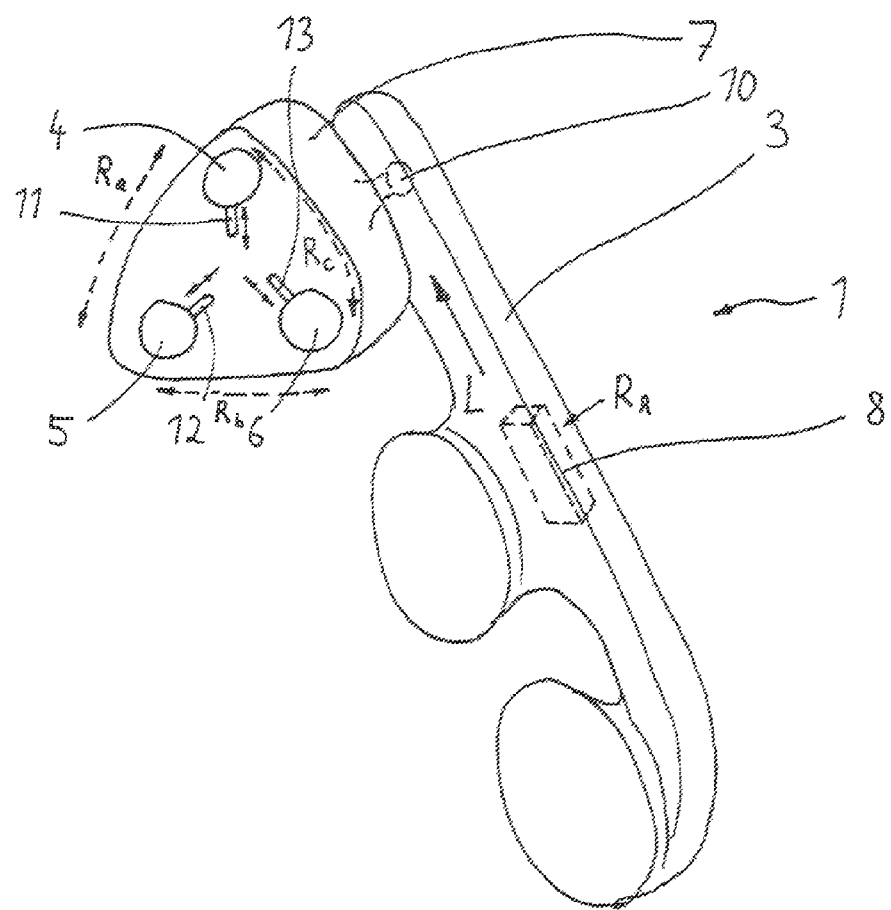

(51) Int. Cl.
  *A61N 1/36* (2006.01)
  *A61N 1/04* (2006.01)
  *A61H 39/00* (2006.01)
  *A61B 5/00* (2006.01)

(52) U.S. Cl.
  CPC ........ *A61B 5/6815* (2013.01); *A61H 2205/027* (2013.01); *A61N 1/0456* (2013.01); *A61H 2201/0184* (2013.01); *A61N 1/0488* (2013.01)

USPC ................ 607/55; 607/62; 607/136; 600/372

(56) References Cited

U.S. PATENT DOCUMENTS

2003/0195588 A1  10/2003  Fischell
2009/0030529 A1*  1/2009  Berrang et al. ................ 623/25

FOREIGN PATENT DOCUMENTS

WO  2008/128270 A2  10/2008
WO  2009/137683 A2  11/2009
WO  2010/032114 A2  3/2010

* cited by examiner

DEVICE AND METHOD FOR APPLYING A TRANSCUTANEOUS ELECTRICAL STIMULATION TO THE SURFACE OF A SECTION OF THE HUMAN EAR

CROSS-REFERENCE TO RELATED APPLICATIONS

This application is a Continuation of PCT/EP2012/001633 filed Apr. 16, 2012, which in turn claims the priority of DE 10 2011 018 228.4 filed Apr. 19, 2011, the priority of both applications is hereby claimed and both applications are incorporated by reference herein.

The invention relates a device for applying a transcutaneous electrical stimulation stimulus to the surface of a section of the human ear, which comprises a retaining element which is mountable on or in the ear and a number of electrodes which are arranged on or in an electrode carrier, wherein the device comprises a control apparatus which controls or regulates the generation of a potential difference between the electrodes, wherein at least three electrodes are arranged on or in the electrode carrier, wherein the at least three electrodes are located in one plane. Furthermore, the invention relates a method for the operation of such a device.

It is generally known to take influence on the neurophysiological and neuroelectrical quality through invasive and noninvasive stimulation of the nerves and thereby on the function of the simulated nerves. Hereby different conditions of sickness can be treated. Numerous devices exist both for the invasive and the non-invasive stimulation.

The present invention is basing upon the method of the transcutaneous electrical stimulation of the nerves. At this method pulse currents of different current forms, amplitudes, pulse durations and frequencies are administered through the skin on different nerves and change their status parameter in an advantageous way.

A device of the above mentioned kind is known from WO 2010/032114 A2. Here, an earphone is described which can be inserted into the ear channel, wherein electrodes are arranged at the earphone to carry out a transcutaneous electro stimulation. Other solutions are disclosed in U.S. Pat. No. 3,659,614, in U.S. Pat. No. 6,341,237 B1 and in WO 2009/137683 A2.

Another device is known from DE 10 2006 023 824 B1. Here, a device for the transcutaneous stimulation of the vagus nerve of the human body is described which can be arranged in this concrete case in the pinna of the ear. The transcutaneous stimulation of the vagus nerve occurs after that parameters of the stimulation current have been pretended. Indeed, the data can be adjusted according to the individual needs. However, after the adjustment the data are fixed. The contact of the tissue which is to be stimulated takes place by two spherical electrodes, which are biased elastically against the skin surface.

It has been found out that the application of transcutaneous stimulation stimuli is beneficial, especially in the region of the Cymba conchae. Thereby, the region of the Cymba conchae is that region of the conchae of the ear which lies above the Crus helicis; it is also called Hemiconcha superior. The region of the Cavum conchae extends downwards below the Crus helicis.

However, in difference to the mentioned DE 10 2006 023 824 B4 it is more difficult here to establish a perfect electrical contact between stimulation electrodes and skin surface. Here, in a specific manner a greasy skin surface or hairiness can exist which aggravates the establishment of a good electrical contact.

Thus, it is an object of the present invention, to provide a device of the mentioned kind as well as a corresponding method which allow in an improved manner to accomplish a safe transcutaneous stimulation. Thereby, it should be determined if applicable in a simple manner that the contact relations of the electrodes on the skin are insufficient.

The solution of this object by the invention is characterized in that the position of at least one of the at least three electrodes is adjustable on the electrode carrier, wherein the at least one electrode of which the position is adjustable is mounted such as to be displaceable in a translational manner in the plane, wherein the electrode carrier is arranged movable relatively to the retaining element so that the electrode carrier can swivel relatively to the retaining element in such a manner that all electrodes are in contact with the skin surface in the region of the Cymba conchae when the retaining element is attached to the ear, wherein between the electrode carrier and the retaining element a spherical joint or a hinge joint is arranged or wherein between the electrode carrier and the retaining element a spring element (preferably designed as a connection section made from long-term flexible material) is arranged.

Preferably, exactly three electrodes are arranged at the electrode carrier.

The mentioned plane corresponds thereby especially at least approximately to the skin surface on which a transcutaneous stimulation stimulus has to be applied.

Thereby, it is preferably provided that three electrodes are arranged triangular on or in an electrode carrier, especially in the form of an equilateral triangle.

Preferably all electrodes are adjustable arranged with respect to their position at the electrode carrier. The at least one electrode which is adjustable in its position is preferably arranged linear movable in a linear guide. Thereby, in adjustability of all electrodes the linear guides are aligned preferably radiating to another, i.e. the electrodes can be displaced radially. Also, at least one of the electrodes can be arranged movable in a guide which runs articulated around a virtual center point; so, this electrode can be moved along a circular path and can be approached and displaced respectively to or from the neighbor electrodes. Thereby, the position of the electrodes becomes adjustable in an optimal way for each individual application.

Preferably, the ability to swivel of the electrode carrier relatively to the retaining element is prevented around a longitudinal axis of the retaining element.

Preferably, the electrodes are designed as hemispherical metal elements; but also other designs are possible.

The method for the operation of such a device for applying a transcutaneous electrical stimulation stimulus onto the surface of a section of the human ear is characterized by the method steps:

a) Measuring of the resistance between each pair of electrodes when the device is arranged at or in the ear for all possible pairs of electrodes by the control apparatus;

b) Comparison of the measured resistances between the pairs of electrodes and selection of the lowest resistance by the control apparatus;

c) Causing of a predetermined transcutaneous stimulation by the control apparatus via that pair of electrodes which have the lowest resistance between them.

Thereby, the control apparatus can compare the measured resistances with a stored reference resistance after carrying out of step a), wherein a signal is issued and/or the stimulation is prevented in the case that all measured resistances are above the stored reference resistance.

Thus, the proposed otoplastic (stimulation device) according to the invention has at least—preferably exactly—three punctual electrodes which are arranged in a plane. Preferably, it should be arranged in the Cymba conchae.

From the control apparatus the electrodes are charged with a stimulation current.

The three punctual electrodes can be arranged like the corner points of a triangle. Thereby, a good rest of all three electrodes on the skin is obtained also with low pressure of the electrode carrier on the skin surface.

The electrode carrier can be equipped, as explained, with a flexible adjustment to the unevenness of the ground (analogue to a rail bogie with a center pivot point by which an adjustment to unevenness is possible). For doing so a solution with a hinge joint or spherical joint can be employed, wherein preferably a restriction of the degree of freedom is provided in such a manner that no axial rotation around the longitudinal axis of the retaining element is possible.

Also, a long-term elastic buffer between electrode carrier and retaining element (pressure bow) with a defined reset force is possible.

The above mentioned method allows the measurement of the contact quality with a contact evaluation at all (three) electrodes; subsequently, an elimination occurs of the electrode which has the worst conductivity and a subsequent stimulation only with the two other electrodes with better conductivity.

The mentioned contact evaluation can occur by means of a fix stored reference value which is stored in the control apparatus.

A possible mode of operation is basing on the simultaneous charging of the especially three electrodes with rotating changes of polarity clockwise or counter-clockwise or stimulation sequences.

Also, a variable arrangement of at least one of the at least three electrodes is beneficial with respect to the distance relatively to the (two) other electrodes. Preferably, such adjustability can be provided for all electrodes. Therefore, the aim is to cover an optimal stimulation scope for each individual ear.

Figure 2:
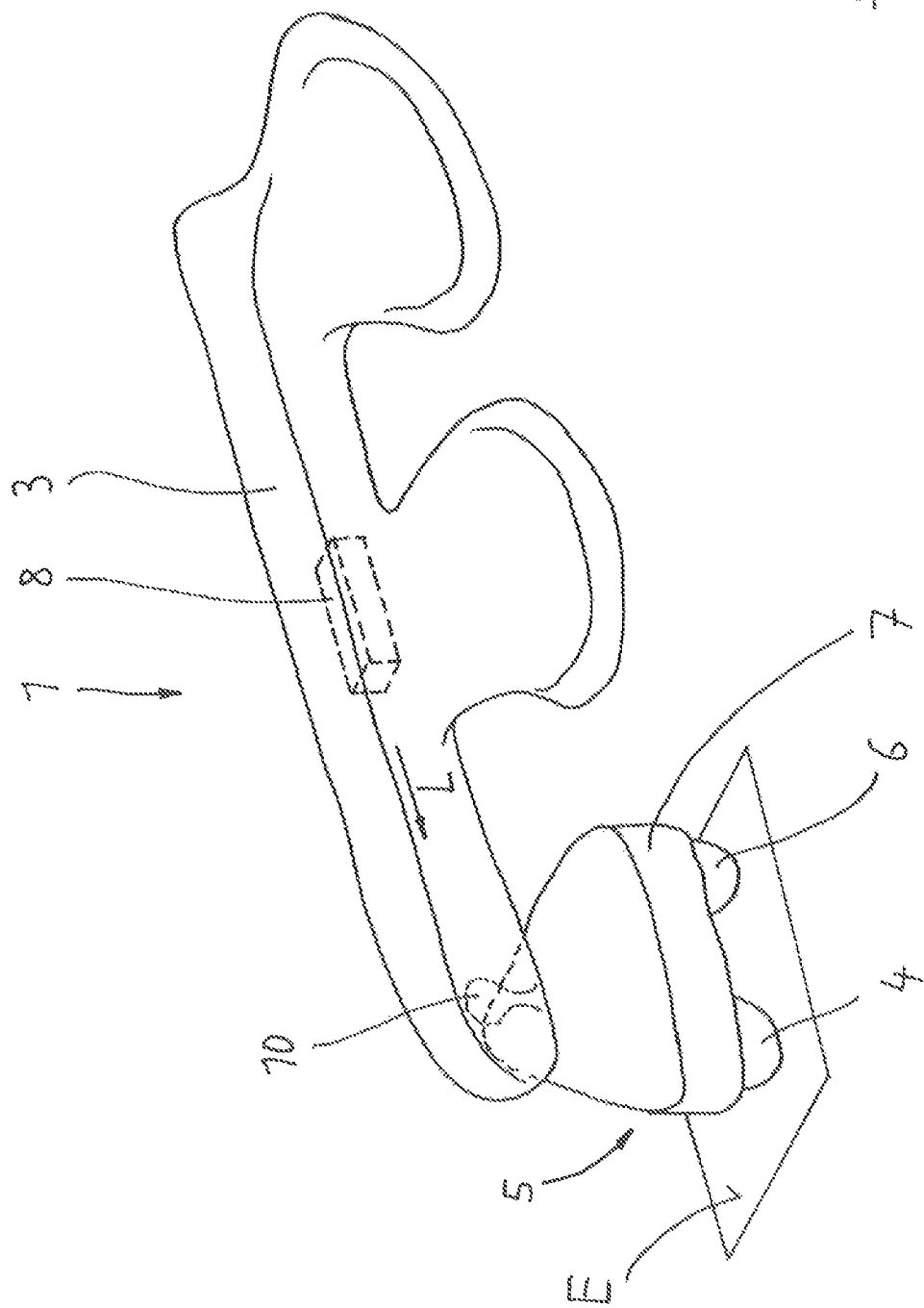
Figure 3:
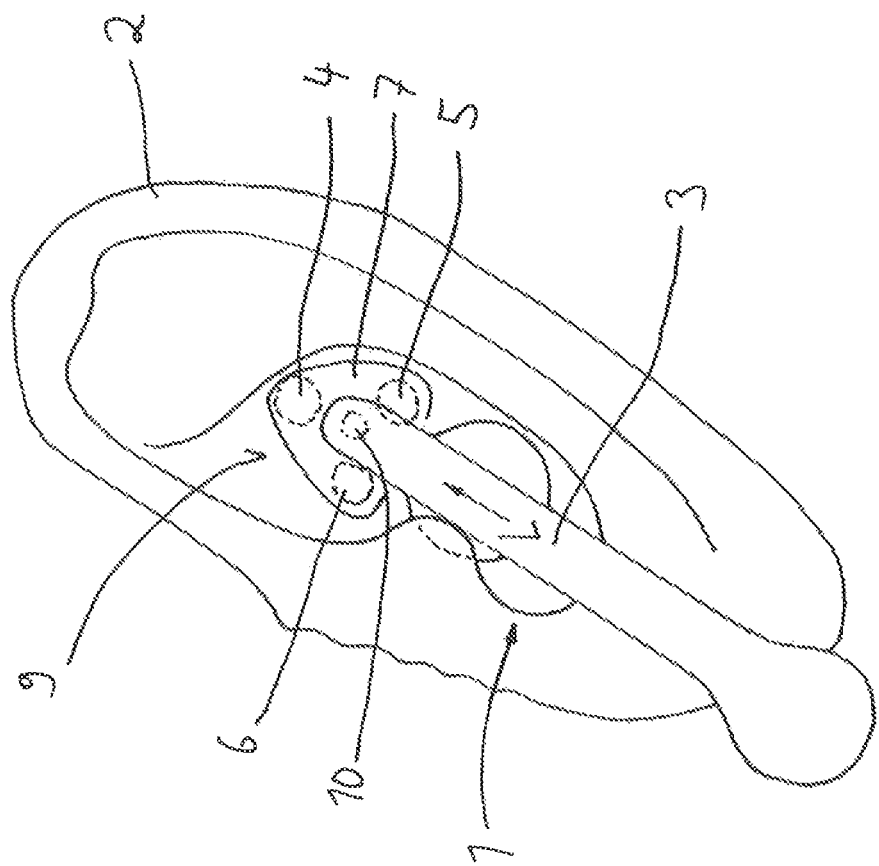

In the drawing an embodiment of the invention is depicted. It shows:

FIG. 1 schematically in a perspective view a stimulation device for the transcutaneous stimulation of the Cymha conchae of a human ear, FIG. 2 schematically in a perspective view the stimulation device according to FIG. 1, seen from another perspective, and FIG. 3 a human ear at which the stimulation device is arranged.

In FIGS. 1 and 2 a device 1 for the transcutaneous stimulation of a section of the human ear is depicted. The device 1 has a retaining element 3 which can be fixed at the ear (see also FIG. 3). The retaining element 3 extents substantially in the direction of a longitudinal axis L. An electrode carrier 7 is arranged at the retaining element 3 which comprises at hand three electrodes 4, 5 and 6. The electrodes are at hand designed as hemispherical structures.

As far as in principle the construction of a vagus nerve stimulation device is concerned the described design corresponds to the pre-known solution according to the above mentioned DE 10 2006 023 824 B4 of the applicant on which insofar explicitly reference is made.

The electrode arrangement is designed to be arranged at the ear of the person which uses the device 1 in the region of the vagus nerve. So, a transcutaneous stimulation of the vagus nerve can be carried out.

As results from in the synopsis of FIG. 1 and FIG. 2 the three electrodes 4, 5, 6 lay in a plane E. They are arranged triangular. This has the benefit that a statically determined rest on the surface to be stimulated is given, whereby all three electrodes 4, 5, 6 lay optimal on the skin surface.

The supply of the electrodes 4, 5, 6 with a stimulation current is caused by a control apparatus 8 which is only denoted schematically.

Furthermore, as can be seen by including of FIG. 3 the device 1 is placed in such a manner in respectively at the ear 2 of a patient that the electrode carrier 7 with its three electrodes 4, 5, 6 lays in the region of the Cymba conchae. The electrode carrier 7 is arranged swivelling relatively to the retaining element 3 by means of a spherical joint 10 in such a manner that it can adapt itself to the skin surface 9 of the ear 2 and the Cymba conchae respectively. Accordingly, the electrode carrier 7 can adapt itself in its position in such a manner that all three electrodes 4, 5, 6 lay optimal onto the skin surface 9.

An optimal adaption of the position of the electrodes 4, 5, 6 to the size of the Cymba conchae will be possible by the fact that the electrodes 4, 5, 6 are arranged adjustable in the direction of the double arrow (see FIG. 1) by means of respective linear guides 11, 12 13. Thereby, the linear guides 11, 12, 13 need not necessarily allow an absolute linear displacement of the electrodes 4, 5, 6; also possible is a slightly articulated displacement of the electrodes which is still substantially linear.

The control apparatus 8, which is in connection via not depicted wires with the electrodes 4, 5 and 6, is designed to identify that pair of electrodes between which the lowest electrical resistance exists. Then, the stimulation occurs via this pair.

For doing so the control apparatus 8 measures the electrical resistance between the at hand three pairs of electrodes prior the actual stimulation, i.e. between the electrodes 4 and 5 (resistance $R_a$), between the electrodes 5 and 6 (resistance $R_b$) and between the electrodes 4 and 6 (resistance $R_c$)—see therefore FIG. 1. In the control apparatus 8 itself a reference resistance $R_R$ is stored.

A proper electro stimulation is possible when in any case one of the resistances $R_a$, $R_b$ and $R_c$ respectively lies below the predetermined reference resistance $R_R$.

The control apparatus 8 is designed to compare after the measurement of the resistances $R_a$, $R_b$ and $R_c$ the values with the reference resistance $R_R$.

If all three measured resistances are higher than the reference resistance inappropriate contact relations are given so that in this case the control apparatus 8 can issue a (warning) signal and/or the control apparatus prevents (precautionary) the generation of a stimulation current. In this case the electrodes must be newly applied, e.g. after cleaning of the region of the Cymba conchae which should be electro stimulated.

LIST OF REFERENCES

1 Device for transcutaneous stimulation
2 Ear
3 Retaining element
4 Electrode
5 Electrode
6 Electrode
7 Electrode carrier
8 Control apparatus
9 Skin surface
10 Spherical joint
11 Linear guide 12 Linear guide
13 Linear guide
E Plane
L Longitudinal axis
$R_a$ Resistance
$R_b$ Resistance
$R_c$ Resistance
$R_R$ Reference resistance

The invention claimed is:

1. A device for applying a transcutaneous electrical stimulation stimulus to the surface of a section of the human ear, comprising:
   a retaining element which is mountable on or in the ear;
   a number of electrodes which are arranged on or in an electrode carrier;
   a control apparatus which controls or regulates the generation of a potential difference between the number of electrodes;
   at least three electrodes of the number of electrodes are arranged on or in the electrode carrier, and the at least three electrodes are located in one plane,
   wherein
   the position of at least one of the at least three electrodes is adjustable on the electrode carrier, and the at least one electrode of the at least three electrodes of which the position is adjustable is mounted such as to be displaceable in a translational manner in the plane,
   wherein the electrode carrier is arranged movable relatively to the retaining element so that the electrode carrier can swivel relatively to the retaining element in such a manner that all electrodes are in contact with the skin surface in the region of the Cymba conchae when the retaining element is attached to the ear,
   wherein between the electrode carrier and the retaining element a spherical joint or a hinge joint is arranged or wherein between the electrode carrier and the retaining element a spring element is arranged.

2. The device according to claim 1, wherein the plane corresponds at least approximately to the skin surface on which a transcutaneous stimulation stimulus has to be applied.

3. The device according to claim 1, wherein three electrodes are arranged triangular on or in an electrode carrier, especially in the form of an equilateral triangle.

4. The device according to claim 1, wherein all electrodes are adjustable arranged with respect to their position at the electrode carrier.

5. The device according to claim 4, wherein the at least one electrode which is adjustable in its position is arranged linear movable in a linear guide.

6. The device according to claim 5, wherein, in adjustability of all electrodes, the linear guides are aligned radiating to another.

7. The device according to claim 1, wherein the spring element is a connection section made from long-term flexible material.

8. The device according to claim 1, wherein the ability to swivel of the electrode carrier relatively to the retaining element is prevented around a longitudinal axis of the retaining element.

9. A method for the operation of a device for applying a transcutaneous electrical stimulation stimulus to the surface of a section of the human ear, wherein the device comprises a retaining element which is arrangeable at or in the ear as well as at least three electrodes which are arranged on or in an electrode carrier, wherein the device comprises a control apparatus which controls or regulates the generation of a potential difference between the electrodes, wherein the method comprises the steps:
   a) measuring of the resistance between each pair of electrodes when the device is arranged at or in the ear for all possible pairs of electrodes by the control apparatus;
   b) comparison of the measured resistances between the pairs of electrodes and selection of the lowest resistance by the control apparatus;
   c) causing of a predetermined transcutaneous stimulation by the control apparatus via that pair of electrodes which have the lowest resistance between them.

10. The method according to claim 9, wherein the control apparatus compares the measured resistances with a stored reference resistance after carrying out of step a) from claim 9, wherein a signal is issued and/or the stimulation is prevented in the case that all measured resistances are above the stored reference resistance.

* * * * *